(12) United States Patent
Guendel

(10) Patent No.: US 7,668,353 B2
(45) Date of Patent: Feb. 23, 2010

(54) METHOD FOR PREPARING THE APPRAISAL OF TOMOGRAPHIC COLON PICTURES

(75) Inventor: Lutz Guendel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 684 days.

(21) Appl. No.: 11/304,693

(22) Filed: Dec. 16, 2005

(65) Prior Publication Data

US 2006/0182328 A1 Aug. 17, 2006

(30) Foreign Application Priority Data

Dec. 17, 2004 (DE) ........................ 10 2004 060 931

(51) Int. Cl.
  *G06K 9/00* (2006.01)
  *A61B 6/00* (2006.01)
(52) U.S. Cl. .......................... 382/128; 382/203; 378/21
(58) Field of Classification Search ................. 382/100, 382/106, 128, 129, 130, 131, 132, 133, 134, 382/154, 168, 170, 181, 190, 199, 203, 224, 382/232, 254, 276, 295, 305; 700/86; 345/423; 378/4, 21, 23, 24
See application file for complete search history.

(56) References Cited

U.S. PATENT DOCUMENTS 4,569,014 A * 2/1986 Kishi et al. .................... 700/86
4,710,876 A * 12/1987 Cline et al. .................. 345/423
6,556,696 B1 4/2003 Summers et al.
7,194,117 B2 * 3/2007 Kaufman et al. ............ 382/128
7,260,250 B2 * 8/2007 Summers et al. ............ 382/128
7,379,572 B2 * 5/2008 Yoshida et al. ............... 382/128
7,454,045 B2 * 11/2008 Yao et al. ..................... 382/128
2003/0223627 A1 12/2003 Yoshida et al.
2004/0141638 A1 7/2004 Acar et al.
2004/0165767 A1 8/2004 Gokturk et al.

FOREIGN PATENT DOCUMENTS

DE 102 54 941 A1 6/2004
WO WO 99/04690 2/1999
WO WO 03/046810 A1 6/2003

* cited by examiner

*Primary Examiner*—Seyed Azarian
(74) *Attorney, Agent, or Firm*—Harness, Dickey & Pierce, PLC

(57) ABSTRACT

A method is for preparing the appraisal of tomographic colon pictures, in particular of CT or MR pictures of the colon, in the case of which both a manual personal search takes place during which the lesions thus detected are confirmed, and a search for lesions carried out by a computer, if appropriate with automatic preliminary confirmation, takes place, the appraising person also rechecking the computer aided preliminary confirmations. In the method, those lesions that have already been classified as known and confirmed after a comparison with the set of the lesions already detected manually are excluded from the set of the lesions detected with computer assistance and that are to be presented again for personal confirmation.

13 Claims, 3 Drawing Sheets

METHOD FOR PREPARING THE APPRAISAL OF TOMOGRAPHIC COLON PICTURES

The present application hereby claims priority under 35 U.S.C. §119 on German patent application number DE 10 2004 060 931.4 filed Dec. 17, 2004, the entire contents of which is hereby incorporated herein by reference.

FIELD

The invention generally relates to a method for preparing the appraisal of tomographic colon pictures, in particular of CT or MR pictures of the colon. In the case of this, for example, both a manual personal search may take place during which the lesions Lmx thus detected are confirmed, and a search for lesions Lcx carried out by a computer, if appropriate with automatic preliminary confirmation, may take place, the appraising person also rechecking the computer aided preliminary confirmations.

BACKGROUND

In virtual colonography, either MR colonography or CT colonography, lesions are searched for either by "leafing through" 2-dimensional images, so-called MPRs, or via a virtual flight through the colon. A combination of the two methods is also frequently used. Suspect structures (=lesions) are then examined more accurately and in the case of a positive result they are appropriately marked and described more accurately in a report. This process is carried out manually, mostly by a doctor with appropriate training.

In parallel therewith, a computer-aided search (computer aided detection, CAD) is carried out in which lesions are detected, for example via a preprogrammed pattern recognition method, if appropriate with the aid of further programmed additional criteria, and likewise marked. These lesions detected with computer assistance must subsequently be reconfirmed again by the doctor in order to ensure on the one hand that no lesions are overlooked, but on the other hand lesions detected by the computer are also to be confirmed by the doctor and are to lead to a therapy only in the case of a positive result.

SUMMARY

An object of at least one embodiment of the invention is to find a method for preparing the appraisal of tomographic colon pictures that excludes double confirmation of the same lesions.

The inventor, with respect to at least one embodiment, has realized the following:

It is possible to distinguish between three categories when searching for lesions in a combined manual and computer assisted fashion:

a. lesion that has been detected manually and not detected by the computer;
b. lesion that has not been detected manually and been detected by the computer; and
c. lesion that has been detected both manually and by the computer.

The examining doctor is frequently interested only in markings of category b. He has no wish to have to reconfirm category c lesions that he has already more accurately determined, confirmed and marked in his report. There is thus a need for a method with the aid of which the results of a computer assisted lesion search are compared with the results of the manual search, and only additional search results are specified for further confirmation. To date, the examining doctor must give more accurate consideration to all the computer results, that is to say the results of categories b and c and, if appropriate, delete double markings.

According to at least one embodiment of the invention, the comparison of the manual diagnostic results and the computer assisted search is carried out in a number of steps. It is assumed in this case that the marks applied manually and by the computer are not located at identical coordinates, but only at closely adjacent ones.

For example, the distance $D(Lcx,Lmx)$ between manually detected lesions Lmx and the lesions Lcx detected by the computer can be determined and entered into a matrix:

$$\begin{array}{cccc} & Lm1 & \cdots & Lm4 \\ Lc1 & D(Lc1, Lm1) & \cdots & D(Lc1, Lm4) \\ \cdots & \cdots & & \cdots \\ Lc5 & D(Lc5, Lm1) & \cdots & D(Lc5, Lm4) \end{array}$$

Matrix entries that are larger than a fixed threshold Dmax can be excluded from the start and need no longer be considered below. Instead of a fixed threshold, it is also possible to work with a variable threshold dependent on the size of the manually detected lesion (for example 100% of the size). However, results with a short distance need not necessarily lead to being able to delete the computer assisted result. The lesions Lcx and Lmx are certainly located close to one another but in different sections of the intestine. Consequently, it is not permissible to delete the lesion Lcx detected by the computer, since it does not correspond to the manually detected lesion Lmx.

In this case, however, the normals through the lesions on the wall of the intestine point in different directions. These lesions therefore need no longer be considered below. As second step, the base area, that is to say the area where the lesion has grown together with the wall of the intestine, is firstly determined. This is not always unambiguously possible, particularly with stalked forms that lie flat against the wall of the intestine. These computer results may not then be deleted and must be presented to the doctor for further confirmation.

As an alternative to distinguishing the lesions by the normal vectors, it is also possible to determine the longitudinal section of the colon to which two adjacent lesions are to be counted. For example, it is possible to examine on which side of the colon wall the central point of the two detected lesions is located and to determine the longitudinal section of the colon associated therewith. It is to be pointed out that it is a normal constituent of computer aided detection to carry out a segmentation in which the surrounding material is separated. It is possible therein to determine a volume, centroid or middle without particular outlay in order to define a central point.

Subsequently, the perpendiculars are to be determined and compared in a third step. If these deviate from one another only slightly, identical lesions are involved and there is no need for the corresponding computer result to be reconfirmed, and it can therefore be deleted from the list.

During virtual colonography, work is frequently carried out using two patient positions. Here, the patients are examined, for example, in prone and dorsal positions. It suffices in this case when a lesion is discovered, confirmed and reported in one or the other position. It is current practice for the doctor to ignore the double manually detected lesions. However, if the computer detects lesions either only in the corresponding position (for example manually in prone position, and by the computer in dorsal position), or in both positions, it is likewise multiple markings that are involved and which the doctor does not wish to see.

Owing to the different anatomy of the colon in prone and dorsal positions, the coordinates of comparable structures in the two corresponding data records are not identical. If they are approximately the same, the method described can likewise be used with other threshold values. If the displacements between prone and dorsal positions are too large, automatic deletion cannot be performed. In the case of doubt, the lesions must be presented for a further confirmation and can be deleted by the doctor should the same lesions be involved.

On the basis of these considerations, in order to avoid double work, the inventor proposes a method, in at least one embodiment, for preparing the appraisal of tomographic colon pictures, in particular of CT or MR pictures of the colon, in the case of which both a manual personal search takes place during which the lesions Lmx thus detected are confirmed, and a search for lesions Lcx carried out by a computer, if appropriate with automatic preliminary confirmation, takes place, the appraising person also rechecking the computer aided preliminary confirmations. Further, those lesions that have already been classified as known and confirmed after a comparison with the set of the lesions Lmx already detected manually are excluded from the set of the lesions Lcx detected with computer assistance and that are to be presented again for personal confirmation.

An advantageous concrete refinement of at least one embodiment of the method provides that at least the following method steps are carried out:

the positions P(Lmx) of the detected lesions Lmx are determined and stored during the manual preliminary confirmation;

during the computer aided automatic preliminary confirmation, the positions P(Lcx) of the detected lesions Lcx are determined and stored in the set M(Lc) of the lesions potentially to be evaluated;

all the distances D(Lcx,Lmx) from the positions P(Lmx) are calculated in relation to all the positions P(Lcx); and thereafter the set M(Lc) of the lesions Lcx potentially to be evaluated are checked as follows for the necessity of a reconfirmation:

if all the distances D(Lcx, Lmx) of a lesion Lcx are greater than a specific value Dmax, a branch is made to checking the next lesion Lcx;

if it is impossible to determine the lesion base B(Lcx) of the considered lesion Lcx, a branch is made to checking the next lesion Lcx;

if the normal direction N(Lcx) of the considered lesion Lcx detected with computer assistance points in a direction other than the normal direction N(Lmx) of the manually detected lesion Lmx with the shortest distance D(Lcx, Lmx) from the considered lesion Lcx, a branch is made to checking the next lesion Lcx;

otherwise, the considered lesion Lcx is deleted from the set M(Lc) of the lesions that are to be evaluated;

all the lesions Lcx that remain in the set M(Lc) of the lesions Lcx that are to be evaluated are presented for manual reconfirmation.

In accordance with the basic idea of the invention, the inventor also proposes a method having the following method steps:

the positions P(Lmx) of the detected lesions (Lmx) are determined and stored during the manual preliminary confirmation;

during the computer aided automatic preliminary confirmation, the positions P(Lcx) of the detected lesions (Lcx) are determined and stored;

all the lesions Lcx, detected by the computer, whose position P(Lcx) exceeds a predetermined distance Dmax in relation to all the positions P(Lmx) of each manually detected lesion Lmx, are taken into the set M(Lc) of the lesion Lcx to be reconfirmed manually; and a determination is made for the remaining lesions Lcx, whose position P(Lcx) lies closer than the predetermined distance Dmax to the position P(Lmx) of a manually detected lesion Lmx, as to whether both closely positioned lesions Lmx and Lcx belong to the same lesion and, in the event of a positive result, this lesion Lcx is removed from the set of the lesions to be reconfirmed, or is not added thereto.

In particular, in the case of the lesions Lcx, whose position P(Lcx) lies closer than the predetermined distance Dmax to the position P(Lmx) of a manually detected lesion Lmx, the association of two positionally close lesions Lmx and Lcx can be checked by determining their appurtenance to a longitudinal colon section, and in the case of the same appurtenance this lesion Lcx is subsequently not counted in the set of the lesions to be manually reconfirmed, all the other lesions Lcx being presented for reconfirmation.

Furthermore, the following method steps can be carried out in order to determine the appurtenance to the same longitudinal colon section of a manually detected lesion Lmx and a lesion Lcx, detected with computer assistance, at a short distance:

a centrally situated point Z(Lmx) in the manually detected lesion Lmx and a centrally situated point Z(Lcx) of the lesion Lcx detected with computer assistance are determined;

the normal vectors N(Lcx) and N(Lmx) to the adjacent colon wall through these centrally situated points Z(Lmx) and Z(Lcx) of the lesions Lmx and Lcx are determined; and if the angle between the two normal vectors N(Lcx) and N(Lmx) exceeds a limiting value, the two lesions Lmx and Lcx are counted as belonging to different longitudinal colon sections and are treated as different lesions.

It is possible here, for example, to regard the geometric centroid of a lesion as its centrally located point, and to regard the connecting line between transition points from a colon wall to the considered lesion as the colon wall.

With reference to judging the coincidence of two lesions, it is possible either to assume a concrete value as a predetermined distance Dmax, or to use a function that is dependent on the size of at least one of the adjacent lesions Lcx and Lmx.

BRIEF DESCRIPTION OF THE DRAWINGS

Additional features and advantages of the invention emerge from the following description of example embodiments with reference to the drawings, reference being made to the fact that only elements essential to the immediate understanding of the invention are shown.

Embodiments of the invention are to be explained in more detail below with the aid of the drawings, use being made of the following reference symbols: 1: first decision point; 2: second decision point; 3: third decision point; 4: deletion of the marking; 5: selection of the next lesion; B: lesion base; C: colon; D(Lcx, Lmx): distance from the lesion detected with computer assistance from the manually detected lesion; Dmax: prescribed maximum distance; Lx: existing lesions; Lcx: lesions detected with computer assistance; Lmx: manually detected lesions; N(Lcx): normal vector of the lesion Lcx; N(Lmx): normal vector of the lesion Lmx; P(Lcx): position of the lesions detected with computer assistance, simultaneously identical to Z(Lcx); P(Lmx): position of the manually detected lesions, simultaneously identical to Z(Lmx); W: colon wall.

In the drawings:

FIG. 1 shows an illustration of a colon section with actually present lesions;

FIG. 2 shows an illustration of the manually detected lesions of the colon section from FIG. 1;

FIG. 3 shows an illustration of the lesions detected with computer assistance from the colon section of FIG. 1;

FIG. 4 shows an illustration of the positions of the lesions detected with computer assistance and manually;

FIG. 5 shows a schematic of the method of selection for the reconfirmation;

FIG. 6 shows an illustration of the lesions that are presented for reconfirmation in accordance with the method according to an embodiment of the invention; and FIG. 7 shows a flowchart for decisions according to the method of selection according to an embodiment of the invention.

DETAILED DESCRIPTION OF THE EXAMPLE EMBODIMENTS

Figure 1:
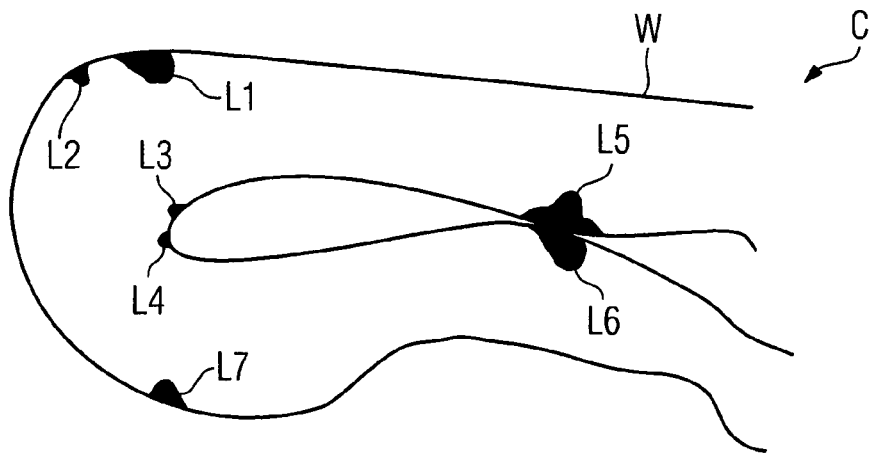

FIG. 1 shows a schematic section of a colon section C having the colon walls W and seven lesions L1 to L7 illustrated by way of example. Critical lesions with reference to the reconfirmation are, on the one hand, the lesions L5 and L6, owing to their spatial proximity in conjunction with appurtenance to different colon sections and, on the other hand, the two lesions L3 and L5 that are relatively close to one another such that the risk also exists here that one of the lesions that has been detected exclusively by the computer assisted search could drop out of the reconfirmation.

Figure 2:
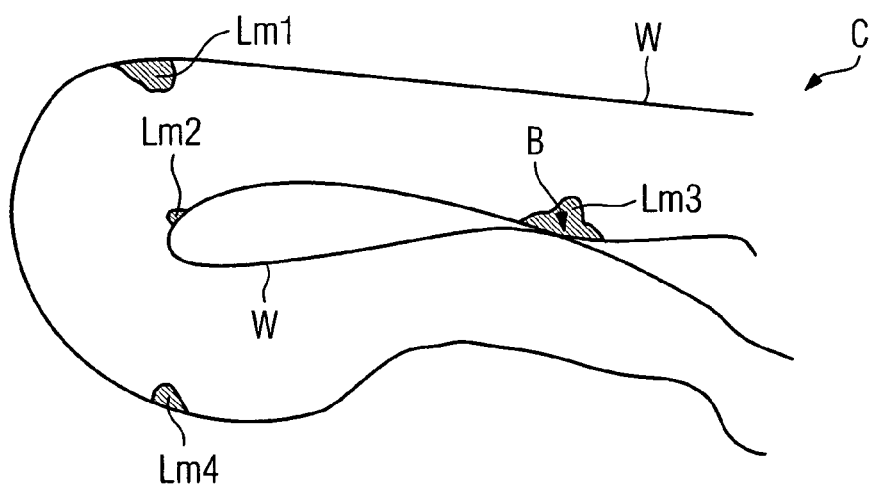
Figure 3:
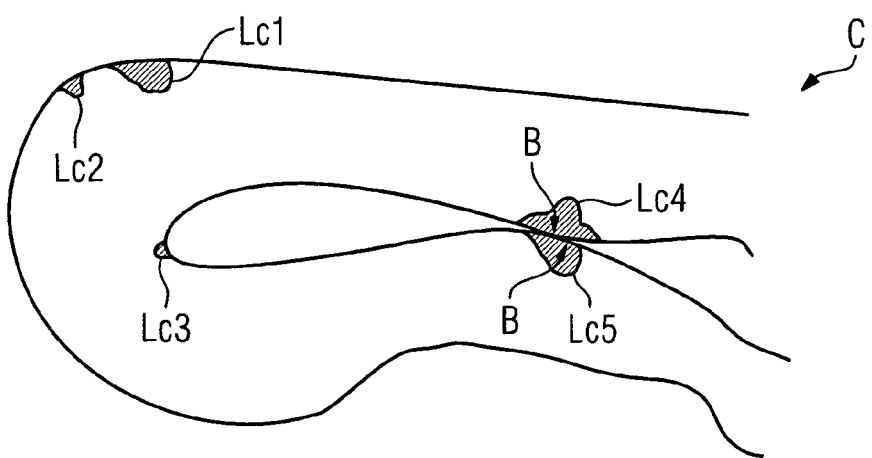

FIG. 2 shows an exemplary result of a manual search. The lesions Lm1 to Lm4 have been detected here and their positions P(Lm1) to P(Lm4) are entered in a database, a list or a matrix. In addition, a computer assisted search for lesions takes place in the colon section illustrated and in which in this example the lesions Lc1 to Lc5, as illustrated in FIG. 3, are detected by the computer. Subsequently, a reconfirmation of all the lesions detected by the computer and not detected in the manual search is to take place.

Figure 4:
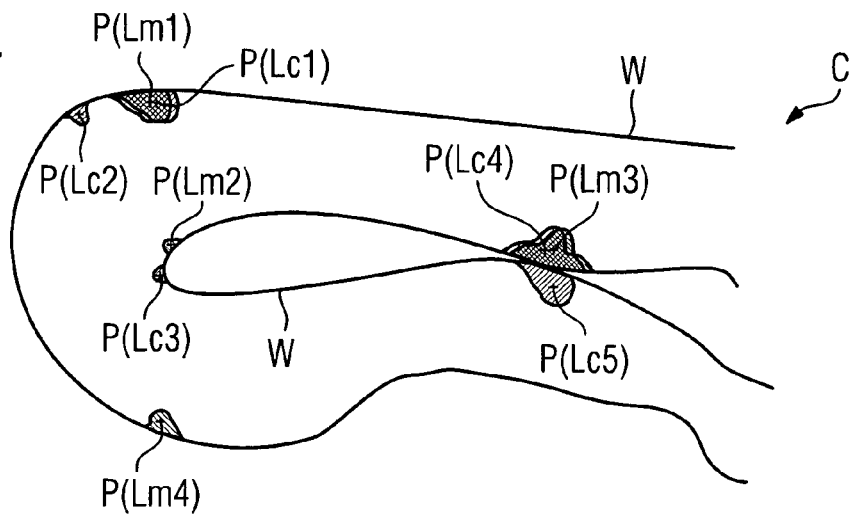

A superposition of the two illustrations of FIGS. 2 and 3 is shown in FIG. 4, which also includes the detected and entered positions P(Lm1) to P(Lm4) and P(Lc1) to P(Lc5). The manually detected lesions are hatched from top left to bottom right, while the lesions detected with computer assistance are hatched from bottom left to top right. Doubly detected lesions are therefore illustrated in FIG. 4 by crosshatching.

An object according to at least one embodiment of the invention is now present of using an appropriate computing method to make available for reconfirmation only those lesions that have been detected by the computer but not detected manually. Involved in the present example are the lesions Lc2, Lc3 and Lc5. In order to identify exactly these lesions, the distances from all the lesions Lmx are respectively calculated for all the lesions Lcx. If a lesion Lcx detected with computer assistance is found that has no further lesions in its vicinity, that is to say at a distance of smaller than Dmax, this lesion is marked for reconfirmation or remains in the set of the lesions to be reconfirmed.

If there is found in relation to a lesion Lcx detected with computer assistance a further lesion Lmx that is located inside the predefined maximum distance Dmax, an attempt must be made to detect whether this lesion actually belongs to the same colon section. There is such a problem in the case of the two lesions Lc5 and Lm3. The lesion Lm3 is located immediately next to the lesion Lc5 detected with computer assistance, such that the lesion Lc5 could drop out of the array of the lesions to be reconfirmed.

However, under the circumstances illustrated, the lesion base of the lesion Lc5 is firstly determined in order to ensure that these two lesions Lc5 and Lm3 are the same lesions. The lesion base B is to be understood as the area or the line at which the lesion is connected to the colon wall W. If this cannot be directly determined, it is possible, for example, to interpolate a line, which can be evaluated as lesion base, at the two-sided transitions between the lesion and the colon wall.

Subsequently, the vertical is dropped onto the lesion base from a central point of the detected lesion Lc5, for example the calculated centroid Z(Lcx), and the direction from the foot of the perpendicular on the lesion base through the central point of the lesions, that is to say the normal vector N(Lcx) of the lesion, is then determined. The procedure is the same for the closest manually detected lesion Lm3 with Z(Lmx), such that a normal vector N(Lmx) is also calculated for the manually detected lesion Lm3.

If the directions of the two normal vectors N(Lcx) and N(Lmx) are now oppositely directed, there are thus two lesions that are to be prescribed to different colon sections such that the lesion Lc5 detected with computer assistance remains in the set of the lesions to be reconfirmed, or is entered in the list of the lesions to be reconfirmed. In the example shown here, the central points Z(Lmx) and Z(Lcx) simultaneously correspond to the positions P(Lmx) and P(Lcx), but this is not necessarily the case.

Moreover, reference may also be made to the two lesions Lc2 and Lm2 lying closely next to one another. These would be considered as identical lesions where a constant maximum distance Dmax is used as decision criterion-as it is used, for example, in the case of the larger lesions Lc1, Lc4 and Lc5. Since the normal thereof also still has the same direction, Lc3 would not be indicated for reconfirmation.

Figure 5:
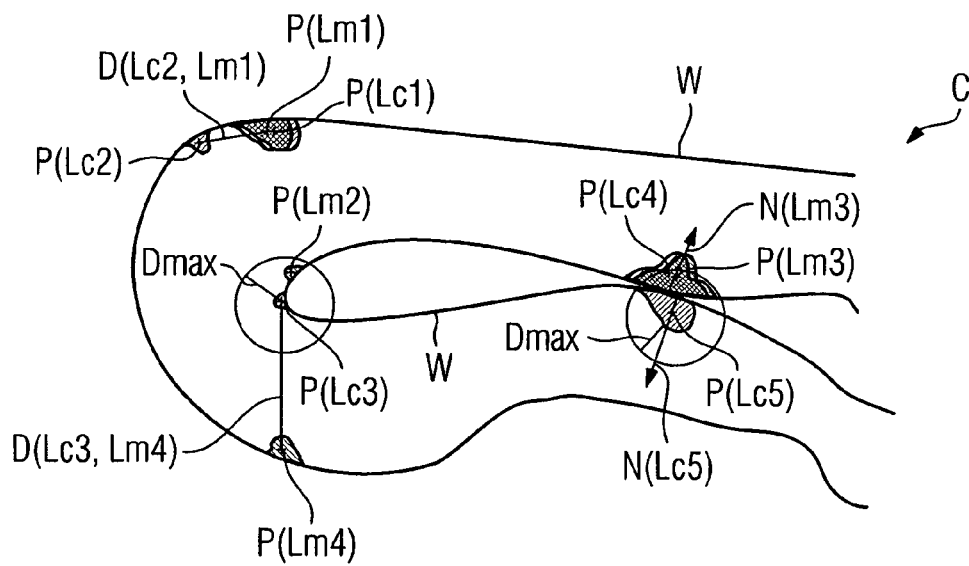

In the illustrated example of the arrangement of the two lesions Lc3 and Lm2, this would lead to an erroneous removal from the reconfirmation. Consequently, it has proved to be particularly advantageous, with reference to the distance criterion, to permit the expansion of the lesion being considered also to play a role. For example, it is possible to determine on the basis of the calculated area of a lesion an adequate radius that reflects approximately the same area as the lesion being considered, and either this radius or a predetermined multiple of this radius is subsequently used as maximum distance. In the case of the lesion Lc3, this would result in the use of a substantially smaller circle than the circumcircle illustrated in FIG. 5, and so an unambiguous separation between the two, lesions Lm2 and Lc3 is rendered detectable, and the lesion Lc3 remains in the set of the lesions to be reconfirmed, or is taken in there.

Figure 6:
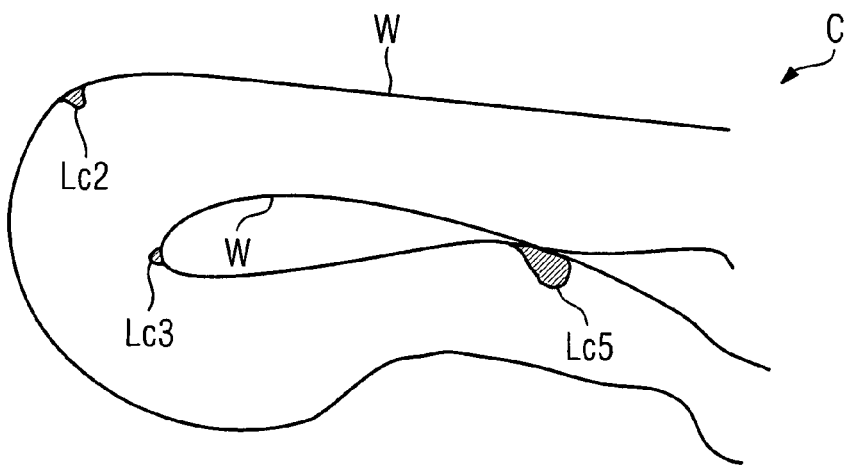

FIG. 6 shows as a result the lesions detected with computer assistance that are to be reconfirmed in accordance with the method according to an embodiment of the invention. The lesions Lc2, Lc3 and Lc5 are involved here. Consequently, the method according to an embodiment of the invention presents the doctor with only three lesions for reconfirmation, while without the method of selection according to an embodiment of the invention the five lesions illustrated in FIG. 3 would be presented overall. Thus, it is to be seen that a substantial easing of the workload takes place thereby.

Figure 7:
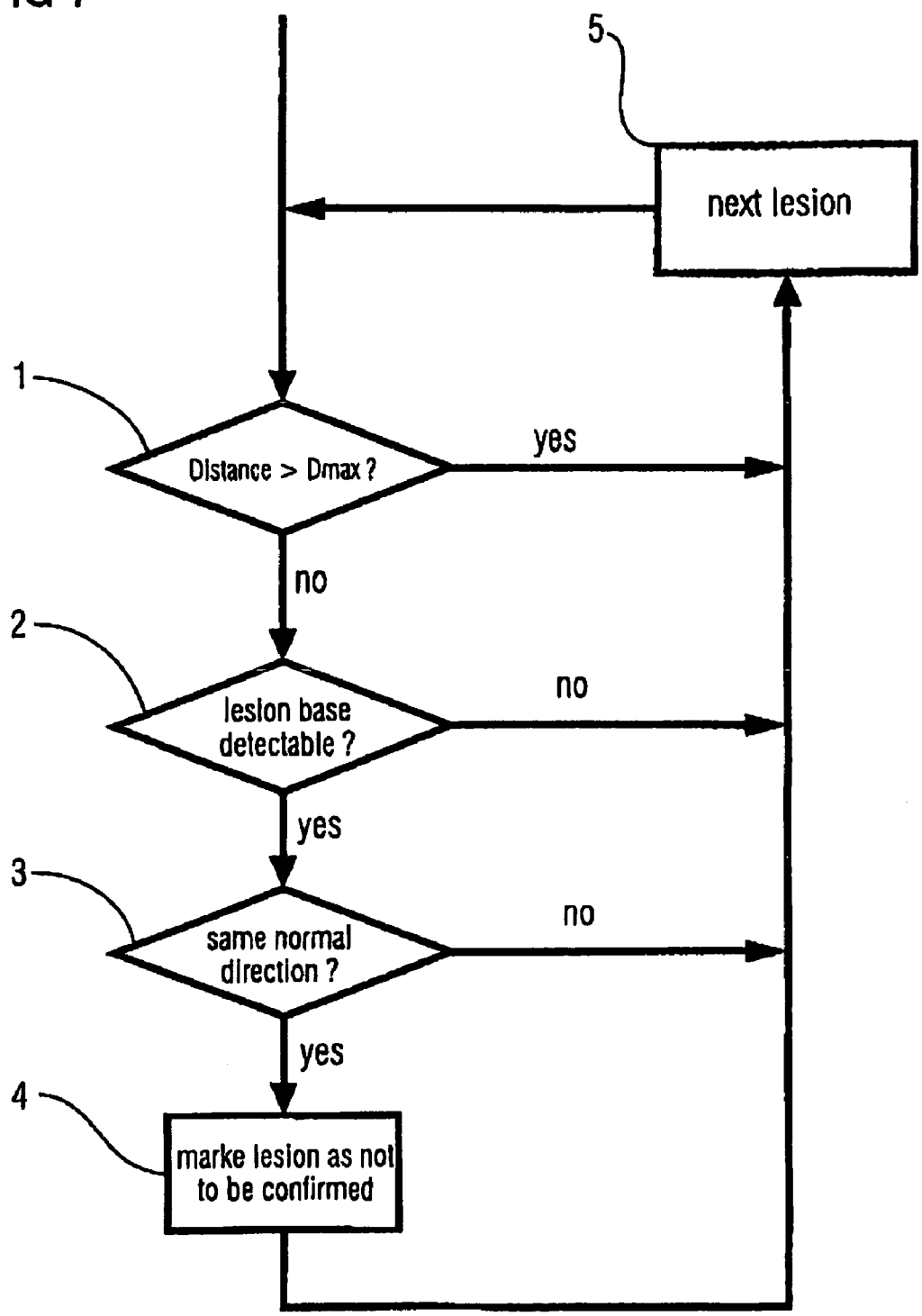

FIG. 7 further illustrates in addition the method cycle in the selection of the lesions to be reconfirmed. The lesions detected with computer assistance are checked in sequence in this case and fed to this decision tree. Here, the distance of the lesion detected with computer assistance from all the others is checked as the first decision point 1.

If each distance is greater than a prescribed distance Dmax, this lesion is entered in the set of the lesions to be reconfirmed, or is not struck out of these, and the next lesion to be checked is selected. If one of the detected distances lies below the specified limit, a branch is made to the decision point 2. An attempt is made to determine a lesion base at the decision point 2. If this cannot be determined, this lesion is also released for reconfirmation, otherwise it is passed on to the decision point 3 at which the normal directions of the two lesions to be compared are determined. If these normal directions are not in the same direction, this lesion is taken over into the set of the lesions to be reconfirmed, or not struck therefrom.

If the normal directions are the same, it is assumed that the same lesions are present here as have already been preconfirmed manually, and so this lesion is finally to be deleted from the set of the lesions to be reconfirmed. Subsequently, the next lesion is fed to this decision tree until all the lesions detected with computer assistance have been checked.

It is self evident that the abovementioned features of the embodiments of the invention can be used not only in the respectively specified combination, but also in other combinations or on their own without departing from the scope of the invention.

Thus, overall, at least one embodiment of the invention excludes from the set of the lesions Lcx detected with computer assistance and that are to be presented again for personal confirmation those lesions that have already been reliably classified as known and confirmed after a comparison with the set of the lesions Lmx already detected manually. It is thereby possible to achieve a substantial reduction in the work required by the diagnosing doctor.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for preparing an appraisal of tomographic colon pictures, in particular of CT or MR pictures of the colon, comprising:
   conducting a manual personal search during which detected lesions of the tomographic colon pictures are confirmed;
   conducting a search for detecting a set of lesions via a computer, with or without automatic preliminary confirmation, the computer aided preliminary confirmations being manually confirmed; and
   excluding lesions that have already been classified as known and confirmed, after a comparison with a set of the lesions already detected manually, from the set of lesions detected with computer assistance and that are to be presented again for personal confirmation, wherein at least the following method steps are carried out:
   determining and storing positions of the detected lesions during the manual preliminary confirmation;
   determining and storing, during the computer aided automatic preliminary confirmation, positions of the detected lesions in the set of the lesions potentially to be evaluated;
   calculating distances from the positions of the manually detected lesions in relation to all the positions of the lesions detected with computer assistance: and
   checking, thereafter, the set of the lesions potentially to be evaluated for the necessity of a reconfirmation, the checking including,
   making a branch, if all the distances of a lesion detected with computer assistance from the manually detected lesion are greater than a specific value, to checking the next lesion detected with computer assistance,
   making a branch, if it is impossible to determine the lesion base of the considered lesion detected with computer assistance, to checking the next lesion detected with computer assistance,
   making a branch, if the normal direction of the considered lesion detected with computer assistance points in a direction other than the normal direction of the manually detected lesion with the shortest distance from the considered lesion detected with computer assistance, to checking the next lesion detected with computer assistance, otherwise deleting the considered lesion, detected with computer assistance, from the set of the lesions detected with computer assistance that are to be evaluated, and
   presenting all the lesions, detected with computer assistance that remain in the set of the lesions detected with computer assistance that are to be evaluated, for manual reconfirmation.

2. The method of claim 1, wherein the predetermined distance is a function of the size of at least one of the adjacent lesions.

3. The method as claimed in claim 1, wherein the method is for preparing an appraisal of at least one of CT and MR pictures of the colon.

4. A method for preparing an appraisal of tomographic colon pictures, in particular of CT or MR pictures of the colon, comprising:
   conducting a manual personal search during which detected lesions of the tomographic colon pictures are confirmed;
   conducting a search for detecting a set of lesions via a computer, with or without automatic preliminary confirmation, the computer aided preliminary confirmations being manually confirmed: and
   excluding lesions that have already been classified as known and confirmed, after a comparison with a set of the lesions already detected manually, from the set of lesions detected with computer assistance and that are to be presented again for personal confirmation, wherein at least the following method steps are carried out:
   determining and storing positions of the detected lesions during the manual preliminary confirmation;
   determining and storing, during the computer aided automatic preliminary confirmation, positions of the detected lesions in the set of the lesions potentially to be evaluated;
   taking all the lesions, detected by the computer, whose position exceeds a predetermined distance in relation to all the positions of each manually detected lesion, into the set of the lesion to be reconfirmed manually; and
   making a determination, for the remaining lesions detected with computer assistance and whose position lies closer than the predetermined distance to the position of a manually detected lesion, as to whether both closely positioned lesions belong to the same lesion and, in the event of a positive result, this lesion is removed from the set of the lesions to be reconfirmed, or is not added thereto.

5. The method as claimed in claim 4, wherein, in the case of the lesions detected with computer assistance, whose position lies closer than the predetermined distance to the position of a manually detected lesion, the association of two positionally close lesions is checked by determining their appurtenance to a longitudinal colon section, and wherein, in the case of the same appurtenance this lesion is subsequently not counted in the set of the lesions to be manually reconfirmed, all the other lesions located with computer assistance being presented for reconfirmation.

6. The method as claimed in claim 5, wherein the geometric centroid of a lesion is used as centrally situated point thereof.

7. The method of claim 6, wherein the predetermined distance is a function of the size of at least one of the adjacent lesions.

8. The method as claimed in claim 5, wherein the connecting line between transition points from a colon wall to the considered lesion is regarded as the colon wall.

9. The method of claim 5, wherein the predetermined distance is a function of the size of at least one of the adjacent lesions.

10. The method as claimed in claim 4, wherein the following method steps are carried out in order to determine the appurtenance to the same longitudinal colon section of a manually detected lesion and a lesion, detected with computer assistance, at a short distance:

- determining a centrally situated point in the manually detected lesion, and a centrally situated point of the lesion detected with computer assistance;
- determining the normal vectors and to the adjacent colon wall through these centrally situated points and of the manually detected lesions and the lesions detected with computer assistance;
- counting, if the angle between the two normal vectors and exceeds a limiting value, the two lesions as belonging to different longitudinal colon sections and treating them as different lesions.

11. The method as claimed in claim 10, wherein the connecting line between transition points from a colon wall to the considered lesion is regarded as the colon wall.

12. The method of claim 10, wherein the predetermined distance is a function of the size of at least one of the adjacent lesions.

13. The method of claim 4, wherein the predetermined distance is a function of the size of at least one of the adjacent lesions.

* * * * *